(12) United States Patent
Ohshima et al.

(10) Patent No.: US 7,567,343 B2
(45) Date of Patent: Jul. 28, 2009

(54) METHOD AND APPARATUS FOR DETECTING DEFECTS ON A WAFER

(75) Inventors: Yoshimasa Ohshima, Yokohama (JP); Sachio Uto, Yokohama (JP); Yukihiro Shibata, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 242 days.

(21) Appl. No.: 11/500,421

(22) Filed: Aug. 8, 2006

(65) Prior Publication Data

US 2007/0070337 A1     Mar. 29, 2007

(30) Foreign Application Priority Data

Sep. 26, 2005   (JP)   ............................ 2005-277051

(51) Int. Cl.
*G01N 21/88* (2006.01)

(52) U.S. Cl. ................................. 356/237.3; 356/237.2

(58) Field of Classification Search ... 356/237.1–237.6, 356/367–369, 625–629; 250/559.42, 559.48, 250/559.45; 359/388, 385, 368; 382/141, 382/145, 149, 245, 266
See application file for complete search history.

(56) References Cited

U.S. PATENT DOCUMENTS

| 5,309,456 | A |   | 5/1994  | Horton |
| 5,486,919 | A | * | 1/1996  | Tsuji et al. .................. 356/484 |
| 5,539,514 | A | * | 7/1996  | Shishido et al. .......... 356/237.4 |
| 5,585,916 | A | * | 12/1996 | Miura et al. ............. 356/237.4 |
| 6,091,075 | A | * | 7/2000  | Shibata et al. .......... 250/559.44 |
| 6,381,356 | B1 | * | 4/2002 | Murakami et al. .......... 382/141 |
| 6,597,446 | B2 | * | 7/2003 | Klooster et al. ......... 356/237.2 |
| 6,693,930 | B1 |   | 2/2004 | Chuang et al. |
| 6,762,831 | B2 | * | 7/2004 | Shibata et al. ............ 356/237.2 |
| 6,813,073 | B2 | * | 11/2004 | Engelhardt et al. .......... 359/388 |
| 6,999,172 | B2 | * | 2/2006 | Masaki et al. ............... 356/364 |
| 7,369,223 | B2 | * | 5/2008 | Hamamatsu et al. ..... 356/237.2 |
| 2005/0052644 | A1 |   | 3/2005 | Lewis et al. |

FOREIGN PATENT DOCUMENTS

JP      2003-130808      5/2003

* cited by examiner

*Primary Examiner*—Sang Nguyen
(74) *Attorney, Agent, or Firm*—Antonelli, Terry, Stout & Kraus, LLP.

(57) ABSTRACT

As circuit patterns become finer in recent years, improvement in detection sensitivity of defects is required. To answer this, sensitivity is being enhanced using a laser with a wavelength of the UV band as the laser for irradiation. A pulse oscillation laser is often used as the UV laser. However, a peak (maximum output) of the pulse oscillation laser becomes very large to an average output power required. For example, in the case of a laser of average output power 2 W, pulse interval 10 ns, and pulse width 10 ps, the peak (maximum output) becomes as high as 2 kW, and there is the possibility of causing a damage to a sample. Therefore, it is necessary to reduce the peak (maximum output) with the average output power being maintained, so that it may not cause a damage to the sample. In this invention, the device is configured in such a way that pulsed light is optically divided into several pulses and these pulses are given respective paths whose lengths are set different from one another, whereby the peak (maximum output) is reduced while the average output value are maintained.

8 Claims, 6 Drawing Sheets

- |||: P polarized light
- •••: S polarized light
- +++: P+S
- ◯: Elliptically polarized light

Rm = Mirror reflectance
Rs = PBS/S polarized light reflectance
Tp = PBS/P polarized light reflectance Ellipticity = $Rm^2 * Rs^2/Tp^2$

$t = L/c$
c: Velocity of light

METHOD AND APPARATUS FOR DETECTING DEFECTS ON A WAFER

BACKGROUND OF THE INVENTION

1. Field of the Invention

This invention relates to a foreign matter and defect detecting apparatus for detecting minute foreign matters and/or defects existing on a semiconductor substrate etc. with high sensitivity and high speed.

2. Description of the Related Art

In production lines of semiconductor substrates, thin film substrates, etc., in order to maintain and improve product yield, there is widely carried out inspection of defects and foreign matters existing on surfaces of semiconductor substrates, thin film substrates, etc. For example, with a sample of a semiconductor substrate etc. before formation of a circuit pattern, it is necessary to detect minute defects and foreign matters (herein after referred to as defects) of a size of 0.05 μm or less on the surface. In the conventional inspecting apparatus, in order to detect such defects, a laser beam of visible light converged to a diameter of a few tens of μm is applied onto the sample surface, and scattered light from the defects are collected and detected. Moreover, with a sample of a semiconductor substrate etc. after circuit pattern formation, the defects are recognized by irradiating a collimated laser beam on the sample surface, collecting the scattered light generated on the sample surface, while diffracted light from a periodical pattern is shaded with a spatial filter, scattered light from the non-periodical pattern and defects is detected, and signals resulting from the non-periodical pattern is eliminated by die comparison.

As an inspecting apparatus that uses UV light having a shorter wavelength than the visible light as a light source, JP 2003-130808 A discloses a method for irradiating a sample using a UV pulsed laser as a light source with a reduced peak of the pulse and an apparatus therefor.

SUMMARY OF THE INVENTION

In recent years, as circuit patterns become finer, improvement of detection sensitivity of defects is demanded. For this purpose, enhancing sensitivity is tried to be attained using a laser having a wavelength in the UV band as a laser for irradiation. Because the quantity of scattered light generated by minute particles of 0.1 μm or less is in inverse proportion to the fourth power of the irradiation wavelength, enhancing sensitivity becomes possible by shortening the wavelength.

As a UV laser, a pulse oscillation laser is often used. However, a peak of the pulse oscillation laser (maximum output) becomes highly large to an average output power that is needed. For example, in the case of a laser of average output power 2 W, light emission frequency 100 MHz, pulse interval 10 ns, and pulse width 10 ps, the peak (maximum output) becomes as high as 2 kW and there is the possibility of causing a damage to a sample. For this reason, it is desirable to reduce the peak (maximum output) while maintaining the average output power.

JP 2003-130808 A discloses a technique of dividing a laser beam emitted from a UV pulsed-laser light source into a plurality of pulses and irradiating them on a sample. However, in JP 2003-130808 A, peaks of the respective divided pulses are set to be reduced gradually, and it was not considered that the maximum of the peak of each pulse after the division was reduced to be as low as possible.

In this invention, the apparatus for detecting defects is configured to be able to divide a laser beam emitted from the UV pulsed-laser light source into a plurality of pulses and apply each pulse on the sample after the division with a maximum of the peak being reduced to be as less as possible.

That is, in this invention, in order to be able to inspect defects of a sample without damaging the sample even when using a pulse oscillation UV laser, the apparatus for detecting defects is configured to comprise: laser-beam light source means; irradiation optical system means for irradiating a laser beam emitted from the laser-beam light source means on the sample obliquely; detection optical system means for collecting and detecting scattered light from the sample irradiated by the irradiation optical system means; and signal processing means for processing a signal obtained by detecting the scattered light from the sample by the detection optical system means to detect defects of the sample; wherein the laser-beam light source means emits a ultra violet pulsed laser beam, and the irradiation optical system means divides each pulse of the pulsed laser beam emitted from the laser beam light source into a plurality of pulses, and this plurality of pulses divided from the pulsed laser beam are transformed into linearly polarized light and applied onto the sample.

Moreover, an apparatus for detecting defects, comprises: laser-beam light source means; irradiation optical system means for shaping a laser beam emitted from the laser-beam light source means and irradiating it onto a linear area on the sample; detection optical system means for forming an optical image with reflected light from the linear area of the sample irradiated by the irradiation optical system means and taking an optical image thus formed; and signal processing means for processing the image obtained by taking the optical image by the reflected light from the sample by the detection optical system to detect defects of the sample, and the apparatus for detecting detects is configured in such a way that the laser-beam light source means emits an ultra violet pulsed laser beam, and the irradiation optical system means divides each pulse of the pulsed laser beam emitted from the laser beam light source into a plurality of pulses and shapes this plurality of pulses divided from the pulsed laser beam and apply them onto the linear area on the sample.

Furthermore, the apparatus that detects defects by irradiating a pulsed laser beam emitted from the pulsed laser beam light source on a sample from an oblique direction, detecting the reflected light from the sample irradiated with the pulsed laser beam from the oblique direction, and processing the signal obtained by detecting the reflected light from the sample is configured in such a way that each pulse of the pulsed laser beam emitted from the laser beam light source is divided into a plurality of pulses and this plurality of pulses of the pulsed laser beam are transformed into linearly polarized light and applied on the sample.

According to this invention, when using a UV laser of pulse oscillation as an irradiation light source, it is possible to reduce a maximum of the peak of the pulse to be applied on a sample by dividing a pulsed beam emitted from the pulsed laser beam light source into a plurality of pulses and making the peaks of this plurality of pulses divided therefrom to be almost the same value, and therefore, it becomes possible to inspect minute foreign matters and defects with stable sensitivity while reducing damages to the sample.

These and other objects, features and advantages of the invention will be apparent from the following more particular description of preferred embodiments of the invention, as illustrated in the accompanying drawings.

BRIEF DESCRIPTION OF THE DRAWINGS

An upper part of FIG. 3 shows a time waveform of pulsed light emitted from the laser light source, and a lower part thereof shows a time waveform of pulsed light after the pulsed light is divided by the pulsed-light division optical system.

DESCRIPTION OF THE PREFERRED EMBODIMENTS

Hereafter, embodiments of this invention will be described.

First Embodiment

An example in which this invention is applied to an apparatus for detecting defects on the surface of a wafer that did not undergo pattern formation.

Figure 1:
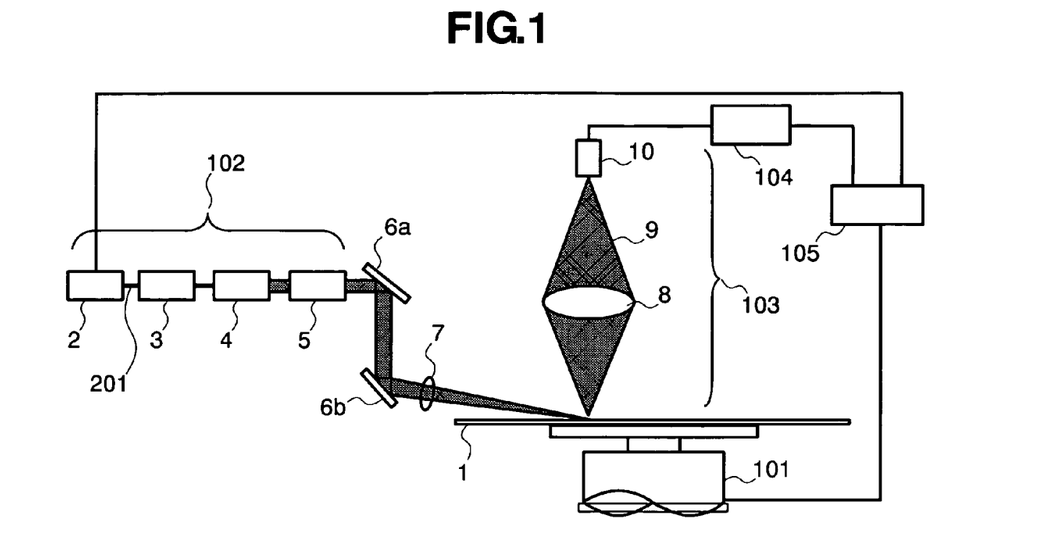
FIG. 1 is a block diagram showing an outline configuration of a first embodiment of an apparatus for detecting defects according to this invention.

FIG. 1 shows one example of an apparatus for detecting defects on a semiconductor wafer before formation of a circuit pattern. FIG. 1 illustrates an outline configuration of the apparatus, which is constructed to comprise an irradiation optical system 102, a detection optical system 103, a wafer stage 101, a signal processing unit 104, and a control unit 105. The irradiation optical system 102 is composed of a laser light source 2, an attenuator 3, a beam expander 4, a pulsed-light division optical system 5, and a converging lens 7. The laser light source 2 is a pulse oscillation laser of a wavelength in the UV (Ultra Violet) region (wavelength region of 400 nm or less). A laser beam 201 emitted from the laser light source 2 is controlled so as to have necessary quantity of light by the attenuator 3, enlarged in beam diameter by the beam expander 4, reduced in peak by the pulsed-light division optical system 5, and subsequently converged and applied onto a detection area on the wafer 1 by the converging lens 7. Mirrors 6a, 6b change an irradiation light path and are used as required.

The detection optical system 103 is composed of a scattered-light detection lens 8 and a photoelectric transducer 10, and uses the scattered-light detection lens 8 to collect almost the whole portion of scattered light 9 from foreign matters on a light receiving surface of the photoelectric transducer 10. Regarding optical processing of the scattered light, for example, by disposing a polarizing plate and a spatial filter between a wafer 1 and the scattered-light detection lens 8 or between the scattered-light detection lens 8 and the photoelectric transducer 10, the optical characteristic can be altered/adjusted, or modified otherwise. The photoelectric transducer 10 generates an electric signal whose magnitude is proportional to the quantity of scattered light. By processing this signal in the signal processing circuit 104, foreign matters and defects are detected and their sizes and locations are found. The photoelectric transducer 10 is used in order to receive and photoelectric-convert the scattered light converged by the detection optical system 103. In the case where the detection optical system 103 is constructed with an imaging optical system, a TV camera, a CCD linear sensor, or a TDI sensor is used; in the case where it is constructed with a converging optical system, a photomultiplier is used.

The wafer stage 101 is composed of a chuck (not shown) for holding the wafer 1, a rotating mechanism (not shown) for rotating the wafer 1, and a translating mechanism (not shown) for translating the wafer 1 in a radial direction. By the wafer stage 101 rotating the wafer 1 in the horizontal plane and translating it in a horizontal direction, it becomes possible to detect foreign matters and defects and their sizes on the whole area of the wafer 1.

The attenuator 3 of this irradiation optical system 102 is constructed with the quarter-wave plate and the polarizing beam splitter (not shown). The emitted beam (linearly polarized light) from the laser light source 2 is transformed into elliptically polarized light by the quarter-wave plate, altering the quantity of light passing through the PBS. By rotating the quarter-wave plate, ellipticity of the polarized light is changed, and accordingly the quantity of light can be adjusted. The beam expander 4 is for enlarging the laser beam 201 emitted from the laser light source 2 in diameter of a cross section perpendicular to an optical axis of the laser beam 201 using a lens system.

Figure 2:
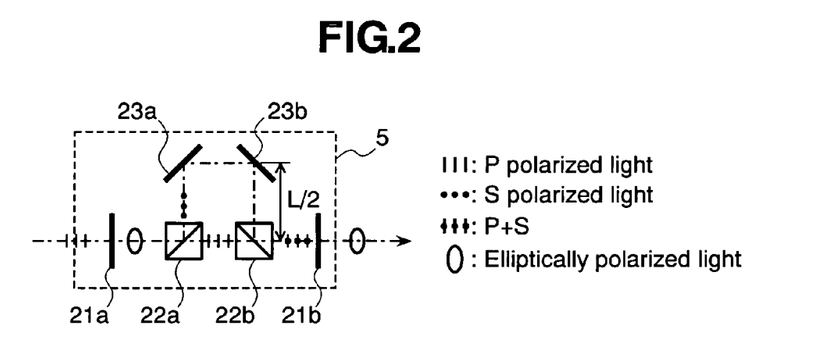
FIG. 2 is a front view showing an outline configuration of a pulsed-light division optical system.

The pulsed-light division optical system 5 is constructed with quarter-wave plates 21a, 21b, PBS's 22a, 22b, and mirrors 23a, 23b, as shown in FIG. 2. The laser beam 201 that is enlarged by the beam expander 4 and enters as linearly polarized light (in this example, P polarized light) is transformed into elliptically polarized light by the quarter-wave plate 21a, and divided into P polarized light and S polarized light by the polarizing beam splitter 22a. P polarized light, one of the divided polarized lights passes through the polarizing beam splitter 22a and the polarizing beam splitter 22b. An S polarized component, the other of the divided polarized lights is reflected by the polarizing beam splitter 22a, the mirror 23a, the mirror 23b, and the polarizing beam splitter 22b, respectively, and returns to the same optical axis as that of a P polarized component having passed through the polarizing beam splitters 22a and 22b. At this time, there occurs an optical path difference of L m between the S polarized component and the P polarized component, where L/2 m is a spacing between the polarizing beam splitter 22a and the mirror 23a and between the polarizing beam splitter 22b and the mirror 23b. Designating the velocity of light by c(m/s), there occurs a time difference between the S polarized component and the P polarized component as written by an expression below.

$$t(s)=L(m)/c(m/s) \quad \text{(Expression 1)}$$

Figure 3:
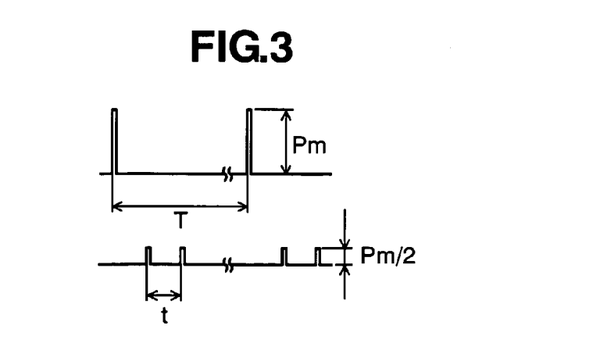

That is, the pulsed light can be time-divided as shown in FIG. 3, and the peak can be reduced to one half.

For example, in the case where a laser of pulse interval 10 ns (10-8 seconds) and pulse width 10 ps (10-11 seconds) and the spacings between the polarizing beam splitter 22a and the mirror 23a and between the polarizing beam splitter 22b and the mirror 23b are set to 15 cm (0.15 m), respectively, the time difference between the S polarized component and the P polarized component becomes 1 ns (10-9 seconds). That is, the laser beam with a half peak will be applied on the wafer surface two times at an interval of 1 ns during 10 ns.

Figure 4:
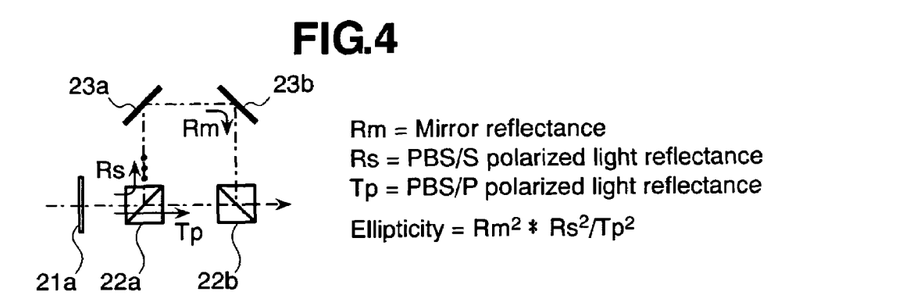
FIG. 4 is a front view showing an outline configuration of the pulsed-light division optical system and explaining ellipticity of the pulsed light having passed through the pulsed-light division optical system.

By adjusting the angle of rotation of the quarter-wave plate 21a, the ratio of the S polarized component and the P polarized component of the incident beam on the polarizing beam splitter 22a is set to 1:1. Because of losses (reflectance, transmittance) of optical components used (the polarizing beam splitters 22a, 22b and the mirrors 23a, 23b), a peak of the pulsed light may differ between the S polarized component and the P polarized component in the outgoing beam of the polarizing beam splitter 22b. In order to lower a maximum of the peak of each pulsed light, it is necessary to adjust the peak of each pulsed light to the almost same magnitude. As shown in FIG. 4, the P polarized component is only affected by P polarization transmittances (Tp) of the polarizing beam splitters 22a, 22b, where as the S polarized component is affected by both the S polarization reflectances (Rs's) of the polarizing beam splitters 22a, 22b and the S polarization reflectances (Rm) of the mirrors 23a, 23b. Designating S polarized component loss by Ls and designating P polarized component loss by Lp, the loss ratio (Pl) is written by $$Pl=Ls/Lp=Rm^2 \times Rs^2/Tp^2. \quad \text{(Expression 2)}$$

Therefore, by adjusting the angle of rotation of the quarter-wave plate 21a so that the ellipticity of the polarization of the incident beam on the polarizing beam splitter 22a may become equal to the above-mentioned loss ratio, the peak value can be made almost equal between pulsed light of the S polarized component and the P polarized component of the outgoing beam of the polarizing beam splitter 22b. The pulsed lights of the P polarized component and the S polarized component so divided that this peak may become almost equal pass through the quarter-wave plate 21b and are transformed into circularly polarized light.

Figure 5:
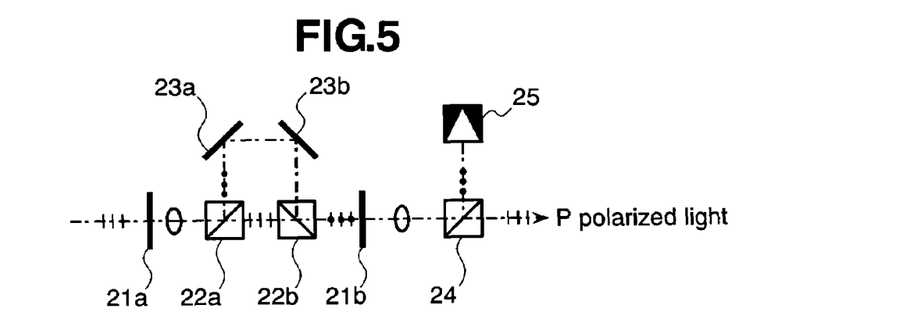
FIG. 5 is a front view showing an outline configuration of the pulsed-light division optical system that is configured to control a polarization state of a pulsed light having passed through the pulsed-light division optical system.

On the other hand, in the inspecting apparatus shown in FIG. 1, normally linearly polarized light is used as the laser beam for irradiating the wafer 1. The laser beam 201 that is transformed into circularly polarized light by the quarter-wave plate 21b can be made to be composed of only the P polarized component by making it pass through a polarizing beam splitter 24, as shown in FIG. 5. Since a reflected S polarized component may act as stray light, it is shaded by a beam trap 25. The peak of the P polarized component that is divided by the polarizing beam splitter 24 and passes through the polarizing beam splitter 24 becomes one half of the peak of the circularly polarized light being incident on the polarizing beam splitter 24. Therefore, the peak of the P polarized component having passed through the polarizing beam splitter 24 is reduced to one fourth compared with the peak of the pulsed laser beam emitted from the laser light source 2.

When using only an S polarized light, what is necessary is to insert a half-wave plate (not shown) after the polarizing beam splitter 24 to effect rotation of polarization direction by 90°. Alternatively, what is necessary is just to rotate the polarizing beam splitters 24 about the optical axis by 90° (in this case, the insertion position of the beam trap 25 is also changed). If the polarization direction is arbitrary, what is necessary is just to use the outgoing beam of the polarizing beam splitter 22b as it is.

Figure 6:
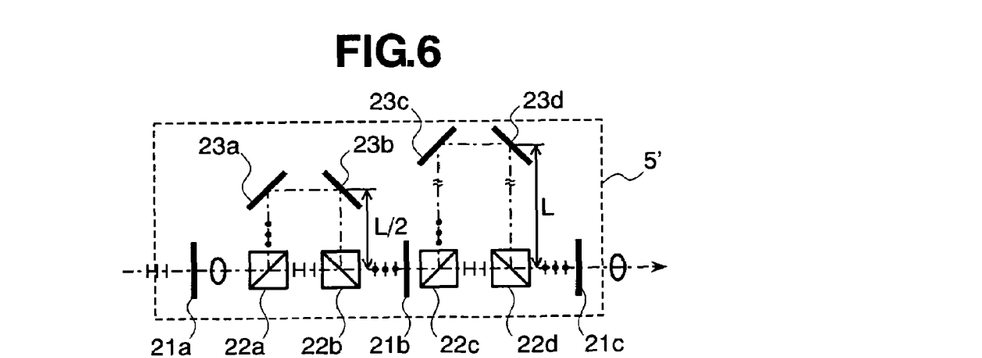
FIG. 6 is a front view showing an outline configuration of the pulsed-light division optical system for dividing one pulse into four pulses.
Figure 7:
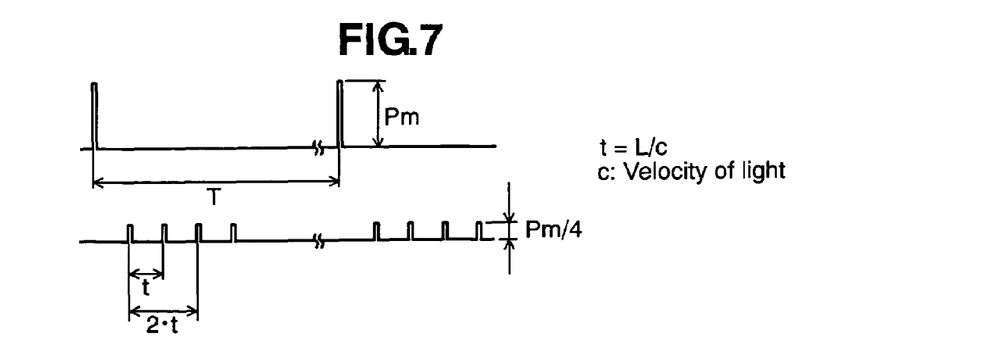
In FIG. 7, the upper part shows a state of pulsed light emitted from the laser light source, and the lower part shows pulsed light after being divided by the pulsed-light division optical system of FIG. 6.

In the above description, a method for dividing a pulsed light into two was explained. A method for dividing into four and a method for dividing into eight will be explained with reference to FIG. 6 and FIG. 8, respectively. The configuration shown in FIG. 6 is a two-stage configuration in which the configuration shown in FIG. 2 is doubly layered. A spacing between a second-stage polarizing beam splitter 22c and a mirror 23c and a spacing between a polarizing beam splitter 22d and a mirror 23d are set to two times the spacing between the first-stage polarizing beam splitter 22c and the mirror 23c and the spacing between the beam splitter 22d and the mirror 23d, respectively. Emitted beams from the first-stage polarizing beam splitter 22b is P polarized pulsed light and S polarized light with a time delay to the P polarized light. By transforming this pulsed light train to circularly polarized light with the quarter-wave plate 21b, the pulsed light train having passed through the quarter-wave plate 21b of an intensity of one half is transformed into P polarized light and passes through the polarizing beam splitters 22c, 22d; where as the pulsed light train having passed through the quarter-wave plate of an intensity of one half is transformed into S polarized light, reflected by the polarizing beam splitters 22c, 22d and by the mirrors 23c, 23d, and returned to the same optical axis. By this optical circuit, the pulsed light is divided into four and each peak is reduced to one fourth, as shown in FIG. 7. Strictly, since the optical parts have losses as described above, each peak decreases to be lower than one fourth.

The P polarized pulsed laser light having passed through the polarizing beam splitter 22d and the S polarized pulsed laser light being reflected thereby proceed on the same optical axis to enter a quarter-wave plate 21c, and are emitted from the quarter-wave plate 21c, being transformed into circularly polarized light, respectively. This circularly polarized light enters the polarizing beam splitter 24 shown in FIG. 5 and is divided into the P polarized component and the S polarized component. The P polarized component is applied on the wafer 1 (the peak of the pulsed beam of the P polarized component divided by the polarizing beam splitter 24 becomes one eighth).

Figure 8:
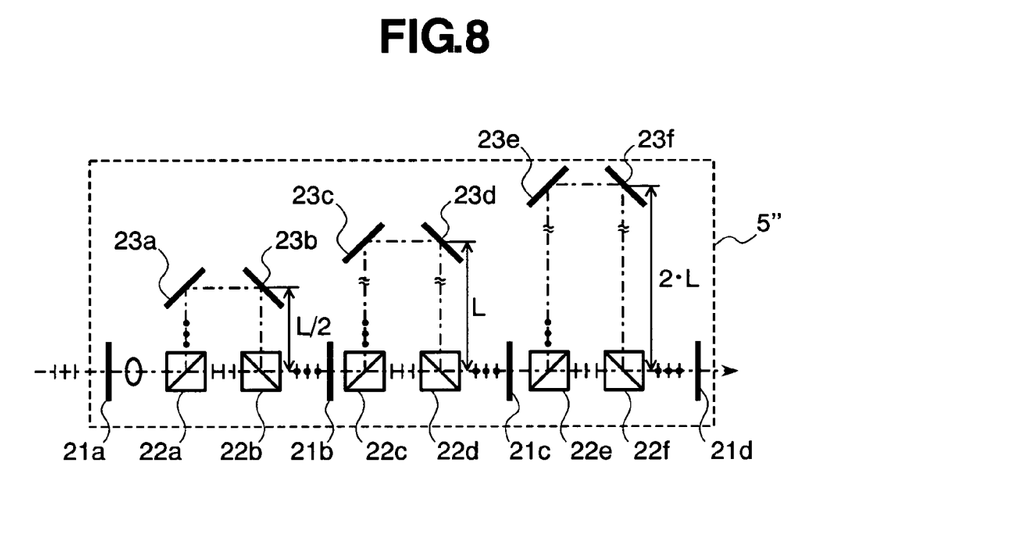
FIG. 8 is a front view showing an outline configuration of a pulsed-light division optical system for dividing one pulse into eight pulses.

FIG. 8 shows a configuration in which the number of division is further increased. That is, the configuration is changed to be of a three-stage type by further adding a configuration of FIG. 2 to the configuration of FIG. 6. A spacing between a polarizing beam splitter 22e (22f) and a mirror 23e (23f) is set to four times the spacing of the first stage. By this setting, by the same operation as the operation explained in the two-stage configuration, the pulsed light is further divided and the peak is reduced to one-eighth. By further increasing the number of stages, the peak can be reduced to $\frac{1}{16}$, $\frac{1}{32}$, $\frac{1}{64}$, .... Restraints in the above-mentioned embodiment are the following two points. The first point is that an optical path difference (L) of the first stage shall be longer than the coherence length ($\Lambda$) of the laser beam used, as written by Expression 3, $$L > \lambda = \lambda^2/\Delta\lambda \quad \text{(Expression 3)}$$

where $\lambda$ is a wavelength and $\Delta\lambda$ is a wavelength bandwidth. The second point is that the divided pulsed light train shall fall within an oscillation interval of the laser, as written by Expression 4, $$L(n+1) < c \cdot (1/f) \quad \text{(Expression 4)}$$

where L is an optical path difference of the first stage, n is the number of stages, c is the velocity of light, and f is an oscillation frequency of the laser.

Figure 9:
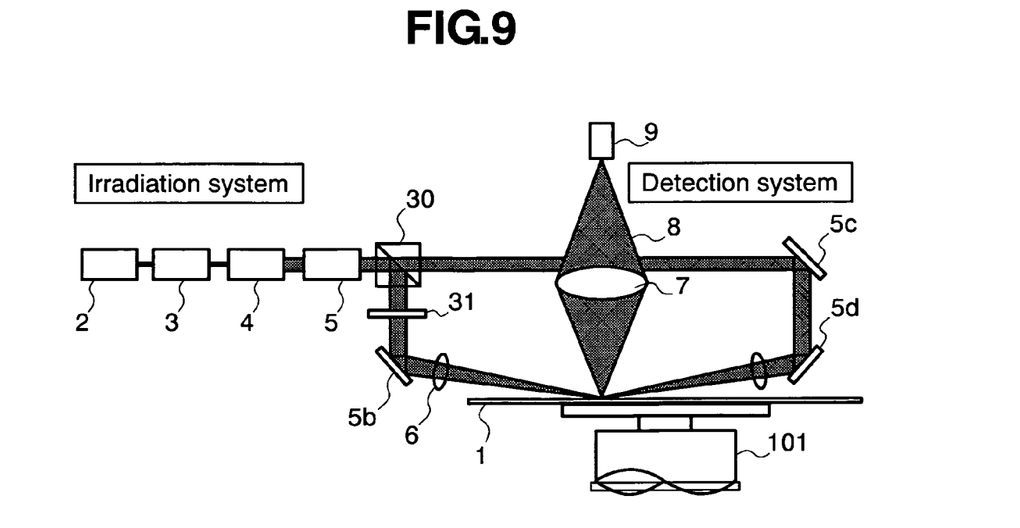
FIG. 9 shows an example of multidirectional irradiation.

Although, in the above-mentioned explanation, a polarization component that is not necessary to obtain linearly polarized light finally is shaded with the beam trap 25, that polarization component can be used for irradiation from two directions, as shown in FIG. 9. For example, in the configuration shown in FIG. 9, a polarizing beam splitter 30 is inserted instead of the polarizing beam splitter 24 in FIG. 5, the P polarized component from the beam in the form of circularly polarized light is made to pass through it and reflected by mirrors 5c, 5d so as to be applied on the wafer 1 obliquely. On the other hand, the S polarized component is configured to be reflected by the polarizing beam splitter 30, transformed into P polarized light by a half-wave plate 31, reflected by a mirror 5b, and applied on the wafer 1 obliquely from anther direction.

Regarding an irradiation direction, both of the two beams are made to be incident on the wafer obliquely at almost the same incidence angle, as shown in FIG. 9. Moreover, depending on an application, the two beams may be set to be incident at different incidence angles. At this time, one of the beams may be incident from a direction almost perpendicular to the wafer 1. Moreover, although the laser beam 201 emitted from the laser light source 2 is finally divided into the two beams and applied on the wafer, the two beams may be divided into three or four and used for irradiation. Moreover, a combination of polarized lights can be freely set by a location of the half wave plate 31 (including selection of use or nonuse).

Since, according to this embodiment, a UV pulsed laser beam can be applied on a wafer with its peak being reduced, it becomes possible to detect extremely minute defects smaller than 0.1 μm without damaging the wafer.

Figure 10:
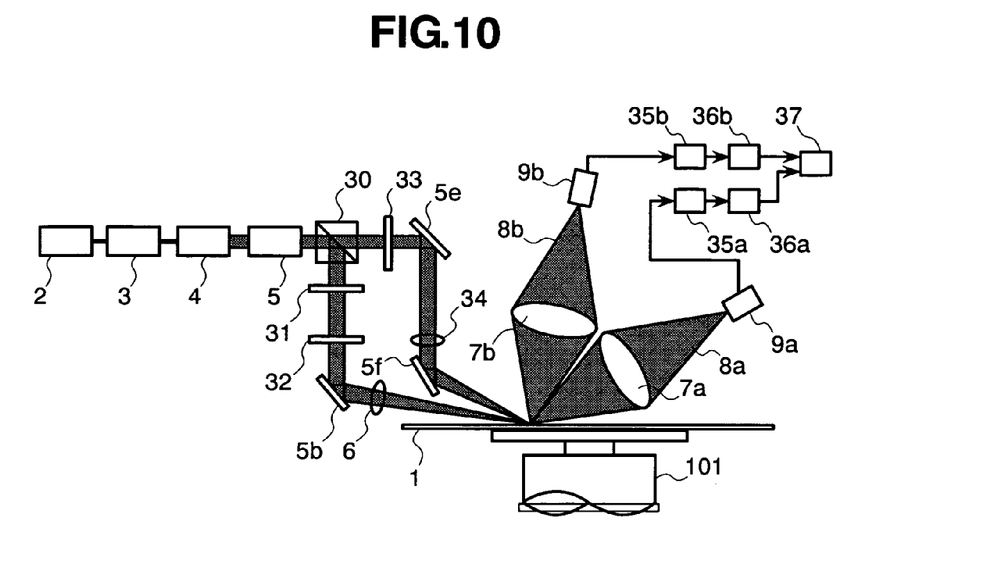
FIG. 10 is a block diagram showing an outline configuration of an irradiation system and a detection system of another example of the multidirectional irradiation.

Next, a method for discriminating irregularities of a defect by applying pulsed laser beams divided by a pulsed-light division optical system on the wafer 1 from multi directions will be explained. As shown in FIG. 10, the polarizing beam splitter 30 divides the beam into P polarized light and S polarized light. The S polarized light, one of the divided polarized lights is transformed into P polarized light by the half-wave plate 31, and irradiation of each pulse beam on the wafer 1 is changed over by opening and shutting of the shutters 32, 33, whereby the wafer 1 is irradiated from two directions having different incidence angles. That is, first, with the shutter 33 being shut, the shutter 32 is opened and the rotating wafer 1 is irradiated with light through the shutter 32. The whole surface of the sample is inspected by moving an irradiation location of the laser beam relatively in a radial direction of the wafer 1 in conformity with rotation of the wafer 1. Scattered light generated during the inspection is converged by a converging lens 7a, and the scattered light 8a thus converged is detected by a photoelectric transducer 9a in synchronization with rotation of the wafer 1. The detected signal undergoes necessary amplification, noise processing, analog-digital conversion in the analog processing circuit 35a. When a defect exists, its detection voltage and existence location (location in an R-Θ coordinate system) are stored in the memory 36a. Subsequently, with the shutter 32 being closed, only the shutter 33 is opened, and the detection is performed. When a defect exists similarly, its detection voltage and existence location are stored in the memory 36b. When two inspections are ended, contents of the memory 36a and contents of the memory 36b are compared: that is, detected voltages of a defect in the same coordinates (tolerance included) are compared to discriminate irregularities. Although in FIG. 10, the detection system is explained as with two systems, if the apparatus has two pieces of memory 36 separately, the detection system may be with one system.

Figure 11:
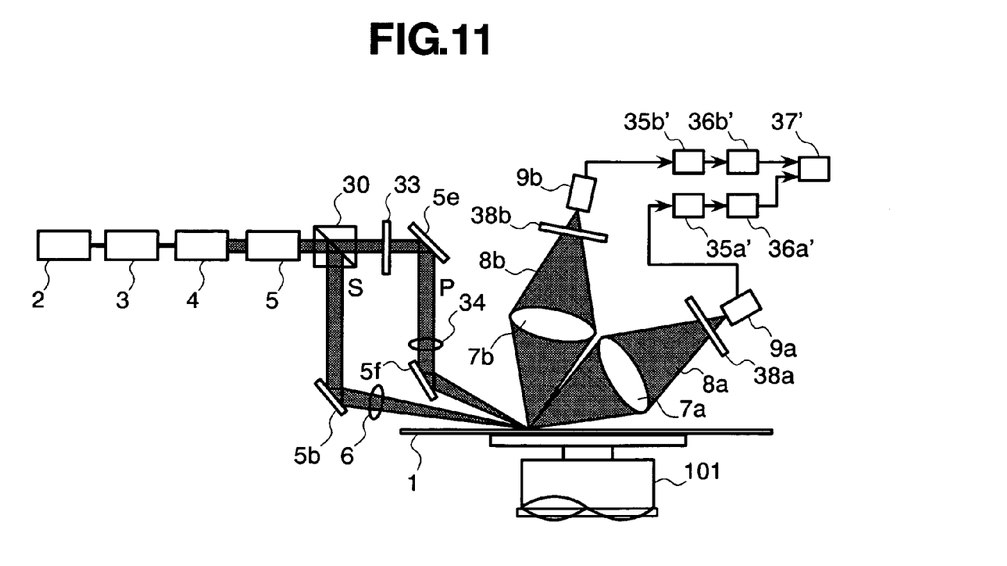
FIG. 11 is a block diagram showing an outline configuration of an irradiation system and a detection system of further another example of the multidirectional irradiation.

FIG. 11 shows another embodiment of a method for discriminating irregularities. The configuration shown in FIG. 11 is the configuration as shown in FIG. 10 from which the half-wave plate 31 is removed. With such a configuration, the S polarization irradiation and the P polarization irradiation are simultaneously performed, and it becomes possible to determine irregularities by detecting the scattered light generated from the surface of the wafer 1 with a polarizing plate 38a and with a polarizing plate 38b independently and comparing these outputs.

Figure 12:
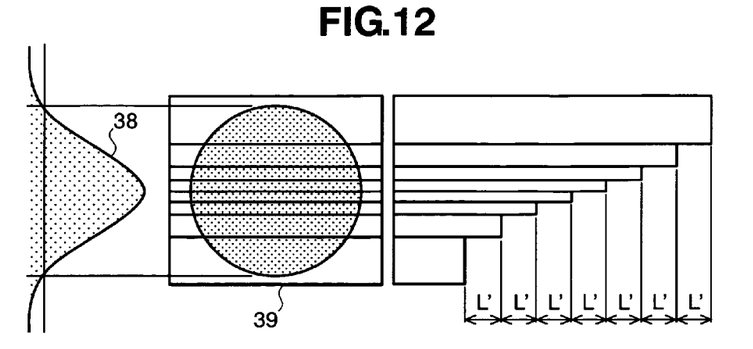
FIG. 12 is a front view showing an outline configuration of a modification example of the pulsed-light division optical system.

FIG. 12 shows another embodiment of the pulsed-light division optical system 5. In this embodiment, in the configuration of the apparatus shown in FIG. 1, the pulsed-light division optical system 5 is substituted with a quartz block 39 (in the case of visible light, optical glass is also usable), and the pulsed beam that was enlarged in cross section by the beam expander 4 is made to enter this quartz block 39 and to divide a single pulse of a laser beam emitted from the laser light source 2 into a plurality of pulses. The number of block stages composed of this quartz block 39 is made equal to the number of division by which a signal pulse of the laser beam 201 emitted from the laser light source 2 is divided, and the lengths of the blocks is set to have a difference of L'. Designating refractive index of quartz by n, the optical path difference between the blocks becomes L'·(n−1), which will come under restrictions of Expressions (3) and (4). Since the laser beam for irradiation is of a Gaussian distribution 38 and normally the center has higher intensity, the thickness of the block is so changed that the quantity of light passing through each block is made equal.

Figure 13:
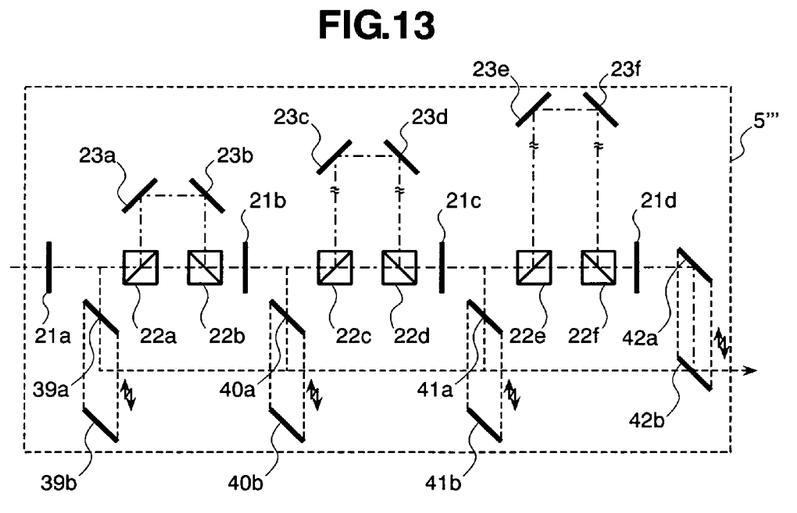
FIG. 13 is a front view showing an outline configuration of the pulsed-light division optical system equipped with a function of selecting the number of division of pulse.

In the pulsed-light division optical system 5" of the inspecting apparatus shown in FIG. 8, FIG. 13 shows an embodiment in which the number of division of the pulsed light is changed in conformity with an inspection target. In FIG. 13, the case where a pulsed-light division optical system 5''' is constructed with three stages will be explained. This embodiment is configured to be able to select the number of division of pulsed light by placing or removing mirrors at an input or output position of each stage. For example, if a pair of mirrors 39a, 39b is inserted before the polarizing beam splitter 22a, a single pulse of the laser beam 201 emitted from the laser light source 2 is applied on the wafer 1 without being divided. Moreover, if a pair of mirrors 40a, 40b is inserted before the polarizing beam splitter 22c, a single pulse of the laser beam 201 emitted from the laser light source 2 is divided and a two-divided pulse train is obtained. Furthermore, if an insertion position of a pair of mirrors is changed to be before the polarizing beam splitter 22e or after the polarizing beam splitter 22f, similarly, a four-divided pulse train or eight-divided pulse train is obtained, respectively.

Figure 14:
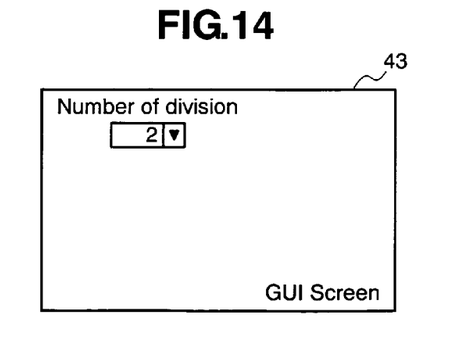
FIG. 14 is an explanatory figure of a GUI screen on which peak reduction is selected.

Moreover, by enabling the number of division to be selected on a GUI screen 43 as shown in FIG. 14, the number of division that matches a sample to be inspected can be set up.

Second Embodiment

Figure 15:
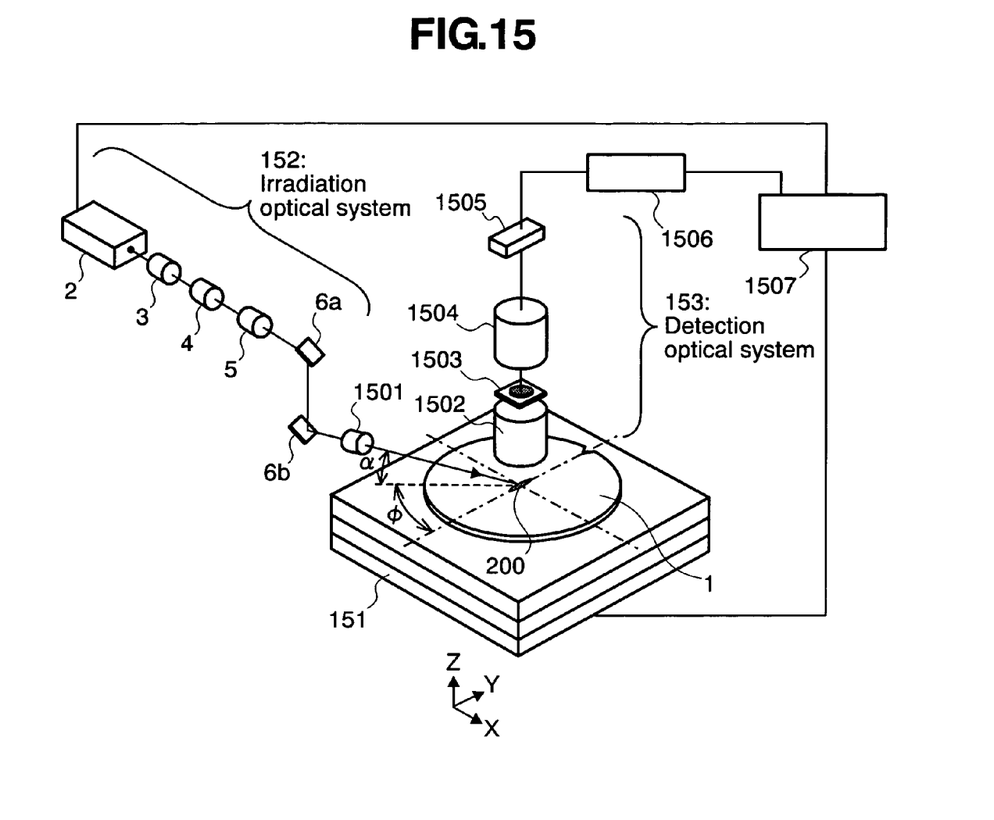
FIG. 15 is a perspective view showing an outline configuration of a second embodiment of the apparatus for detecting defects according to this invention.

FIG. 15 shows an example in which this invention is applied to an apparatus for inspecting a wafer on which a pattern has been formed. An irradiation optical system 152 is almost of the same configuration as that shown in FIG. 1. That is, the irradiation optical system 152 has the laser light source 2, the attenuator 3, the beam expander 4, the pulsed-light division optical system 5, the mirrors 6a, 6b for selecting an irradiation light path, and a converging lens 1501. The pulsed-light division optical system 5 can also take such a configuration as is explained in FIG. 6, 8, or 13.

A detection optical system 153 has a Fourier transform lens 1502, a spatial filter 1503, an inverse Fourier transform lens 1504, and a photoelectric transducer 1505. For the photoelectric transducer 1505, a CCD sensor or TDI sensor is used. A signal processing unit 1506 processes a signal detected by the photoelectric transducer 1505 and thereby defects are detected.

An irradiation area 200 on the wafer 1 irradiated by the irradiation optical system 152 takes the shape that is longer in one direction than in other direction (herein after referred to as linear) in conformity with a detection field of view of the detection optical system 153. Specifically, this linear irradiation area 200 takes the shape of an area elongated in the Y direction perpendicular to the X direction along which a table 151 moves continuously.

Figure 16:
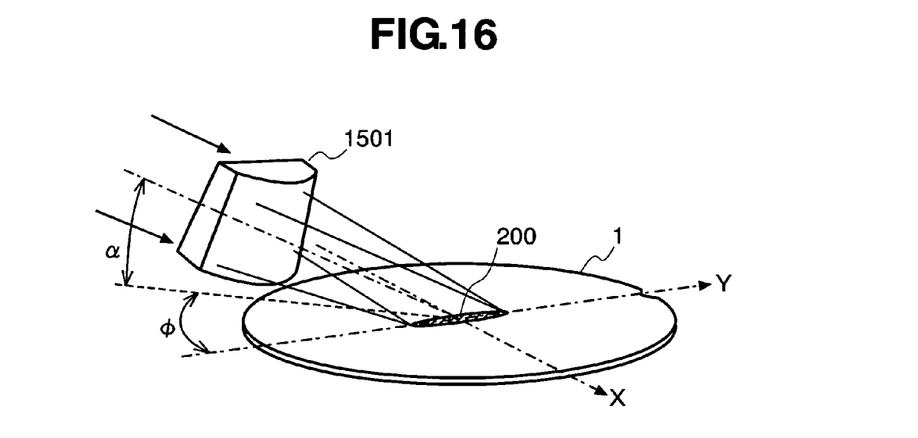
FIG. 16 is a perspective view of a linear oblique irradiation unit of the irradiation optical system and a wafer in the second embodiment of the apparatus for detecting defects according to this invention.

FIG. 16 shows one embodiment of an optical system that realizes liner irradiation. The cylindrical lens 1501 shown in FIG. 16 allows the laser beam 201 that is enlarged in a diameter of a section perpendicular to the optical axis by the beam expander 4 of the irradiation optical system 152 shown in FIG. 15 and is divided into a plurality of pulses (for each input pulse) by the pulsed-light division optical system to enter itself, collects them in one direction, converts to a collimated beam in a direction perpendicular thereto, and applies the collimated beam on the wafer 1. At this time, by setting the laser beam emitted from the cylindrical lens 1501 to be applied on the wafer 1 with an angle φ to the X axis direction of the wafer 1, a portion of diffracted light from a pattern of linear lines along the X direction or the Y direction on the wafer 1 in FIG. 16 entering the Fourier transform lens 1502 can be reduced in quantity (because the majority of patterns on the wafer 1 run in directions making 0° or 90° to the X axis direction of the wafer 1). In order to perform irradiation along the centerline of the sample, the cylindrical lens 1501 whose focal length varies continuously that has an angle φ and an elevation angle α to a sample centerline is used. The sample 1 undergoes whole surface inspection being scanned with a XYZΘ stage.

A method for detecting defects on the wafer 1 on which a pattern has been formed using the optical system explained with reference to FIG. 15 will be explained.

First, the pulsed laser beam 201 emitted from the laser light source 2 is enlarged by the beam expander 4 in diameter of a cross section perpendicular to the optical axis. One pulse of the beam 201 is divided into a plurality of pulses by any one of the pulsed-light division optical system 5 shown in FIG. 2, the pulsed-light division optical system 5' shown in FIG. 8, and the pulse-light division optical system 5" shown in FIG. 13 and incident on the cylindrical lens 1501 after the division. Then the pulses are applied onto a linear area with a longitudinal axis lying in the Y direction on the wafer 1 placed on the table 151 that is controlled by a control unit 1507 and continuously moved in the X direction.

This irradiation generates scattered light from the wafer 1 on which the pattern has been formed. Diffracted light from a pattern having a comparatively short period pitch, for example, a pattern in a memory part, among patterns formed on the wafer 1 forms a diffracted light pattern on a Fourier transform plane of the Fourier transform lens 1502. This diffracted light pattern is shaded with a spatial filter 1503 disposed at the Fourier transform plane of the Fourier transform lens 1502. On the other hand, scattered light from a long period pattern of the order of a die pitch of a large number of dies that are formed on the wafer 1 as well as random scattered light from defects etc. are formed into an image by the inverse Fourier transform lens 1504 without being shaded by the spatial filter 1503. This optical image thus formed is detected by the photoelectric transducer 1505 in synchronization with movement of the table 151 in the X direction. That is, each time the formed optical image moves by 1 pixel pitch on the photoelectric transducer 1505, the photoelectric transducer 1505 picks up an optical image.

In the signal processing unit 1506 connected to the photoelectric transducer 1505, defects are detected by eliminating information of a long period pattern that has not been erased by the spatial filter 1503 by die comparison, namely, by comparing an image that the photoelectric transducer 1505 has obtained by detection in synchronization with movement of the table 151 in the X direction and image picked up in a location where the same pattern is formed in an adjacent die or neighboring die and stored.

Note here that since the pulsed laser beam 201 applied on the wafer 1 is a UV laser whose wavelength is shorter than 400 nm, resolution of foreign matter detection improves compared with the case where visible light is used, which enables foreign matter defects whose sizes are less than 0.1 μm to be detected by differentiating them from a pattern formed on the wafer 1. Further, in this case, since each pulse of the pulsed laser beam 201 emitted from the laser light source 2 is divided into a plurality of pulses by the pulsed-light division optical system 5, the peak of the each pulse is reduced. Consequently, a damage on the wafer 1 can be prevented from being caused.

In addition, when a configuration described with reference to FIGS. 9-11 is adopted as the irradiation optical system 152 and the detection optical system 153, it becomes possible to discriminate a kind and sizes of a detected defect by comparing detected signals that correspond to the respective irradiation or detection in each of which a state of polarization, an irradiation angle, and a detection angle are different.

The method for detecting defects on a wafer by applying a pulsed laser beam that is made into a linear shape and is composed of divided pulses on the wafer explained in this embodiment can also be applied to the case of detecting defects on the surface of a wafer that has not undergone formation of the pattern explained in the first embodiment. At this time, the pulsed laser beam being made into a linear shape is applied on the wafer 1 so that its longitudinal direction may coincide with a radial direction of the wafer 1. An image of the wafer surface irradiated with this pulsed laser beam being made into a linear shape is formed by an imaging optical system and picked up by the CCD sensor in synchronization with rotation of the wafer 1.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for detecting defects, comprising:
a laser-beam light source which emits an ultraviolet pulsed laser beam;
an irradiation optical unit which expands a diameter of the ultraviolet pulsed laser beam with a beam expander, converts a shape of the ultraviolet pulsed laser beam to be converged in one direction and collimated in another direction with a cylindrical lens and obliquely irradiates a linear area of a specimen;
a detection optical unit that forms an optical image by a light reflected from the linear area of the specimen irradiated by the irradiation optical unit and picks up the formed optical image with an image sensor; and
a signal processing unit which processes the optical image obtained with the image sensor to detect defects of the specimen, including defects having sizes less than 0.1 µm;
wherein the irradiation optical unit divides the ultraviolet pulsed laser beam emitted from the laser beam light source into a plurality of pulses and converts the shape of the plurality of pulses, using the cylindrical lens, to irradiate the linear area on the specimen.

2. The apparatus for detecting defects according to claim 1, wherein
the irradiation optical unit divides each pulse of the ultraviolet pulsed laser beam emitted from the laser-beam light source and passed through the beam expander into a plurality of pulses, transforms the plurality of pulses divided from the ultraviolet pulsed laser beam into a plurality of beams of linearly polarized light, converts the shape of the plurality of linearly-polarized ultraviolet pulsed laser beams by a cylindrical lens and obliquely irradiates the linear area on the specimen.

3. The apparatus for detecting defects according to claim 1, wherein
the detection optical unit has a spatial filter for shading scattered light from a pattern formed on the specimen irradiated with the plurality of pulses divided from the ultraviolet pulsed laser beam.

4. The apparatus for detecting defects according to claim 1, wherein
the irradiation optical unit divides each pulse of the ultraviolet pulsed laser beam emitted from the laser-beam light source into a plurality of pulses whose peak levels are almost equal.

5. A method for detecting defects, comprising the steps of:
emitting an ultraviolet pulsed laser beam from a laser beam light source;
expanding the diameter of the ultraviolet pulsed laser beam with a beam expander;
obliquely illuminating a specimen with the ultraviolet pulsed laser beam emitted from the pulsed laser beam light source
detecting light reflected light from the specimen with an image sensor; and
detecting defects of the sample, including defects having sizes less than 0.1 µm, by processing a signal obtained by detecting the light reflected light from the specimen;
wherein each pulse of the ultraviolet pulsed laser beam emitted from the laser beam light source is divided into a plurality of pulses, and the plurality of pulses divided from the ultraviolet pulsed laser beam are converted in shape to be converged in one direction and collimated in another direction by using a cylindrical lens to illuminate a linear area on the specimen.

6. The method for detecting defects according to claim 5, wherein
the specimen is illuminated while being rotated.

7. The method for detecting defects according to claim 5, wherein
during the step of detecting light, the light reflected from a pattern formed on the sample among reflected light from the sample irradiated obliquely with the pulsed laser beam is shaded with shading means, and
the reflected light from the sample that has not been shaded with the shading means is detected.

8. The method for detecting defects according to claim 5, wherein during the step of obliquely illuminating,
each pulse of the pulsed laser beam emitted from the laser beam light source is divided into a plurality of pulses whose peak levels are almost equal.

* * * * *